United States Patent [19]

Phan et al.

[11] Patent Number: 5,859,292
[45] Date of Patent: Jan. 12, 1999

[54] PREPARATION OF HIGH PURITY SODIUM (S)-2(6-METHOXY-2-NAPHTHYL) PROPIONATE

[75] Inventors: Hao V. Phan, Columbia; Robert E. Young, West Columbia, both of S.C.

[73] Assignee: Albemarle Corporation, Richmond, Va.

[21] Appl. No.: 988,796

[22] Filed: Dec. 11, 1997

[51] Int. Cl.$^6$ .................................................. C07C 63/34
[52] U.S. Cl. ............................................................ 562/467
[58] Field of Search ............................................. 562/467

[56] References Cited

U.S. PATENT DOCUMENTS

| | | | |
|---|---|---|---|
| 3,228,831 | 1/1966 | Nicholson et al. | 167/53 |
| 3,385,886 | 5/1968 | Nicholson et al. | 260/515 |
| 3,562,336 | 2/1971 | Nelson | 260/613 |
| 3,651,106 | 3/1972 | Harrison | 260/429 R |
| 3,651,149 | 3/1972 | Harrison | 260/606.5 B |
| 3,652,683 | 3/1972 | Harrison | 260/612 D |
| 3,683,015 | 8/1972 | Dyson | 260/520 |
| 3,686,183 | 8/1972 | Dyson | 260/284 |
| 3,828,033 | 8/1974 | Nelson | 260/240 R |
| 3,904,682 | 9/1975 | Fried et al. | 260/520 |
| 3,904,683 | 9/1975 | Day et al. | 260/520 |
| 3,959,364 | 5/1976 | Armitage et al. | 260/515 R |
| 3,975,432 | 8/1976 | Alvarez | 260/520 R |
| 3,978,116 | 8/1976 | Fried et al. | 260/500.5 H |
| 3,988,365 | 10/1976 | Gallegra | 260/520 D |
| 4,001,301 | 1/1977 | Fried et al. | 260/473 F |
| 4,009,197 | 2/1977 | Fried et al. | 260/473 F |
| 4,239,914 | 12/1980 | Campolmi et al. | 562/466 |
| 4,245,116 | 1/1981 | Ohno et al. | 562/401 |
| 4,246,164 | 1/1981 | Felder et al. | 260/501.17 |
| 4,246,193 | 1/1981 | Holton | 260/501.17 |
| 4,395,571 | 7/1983 | Dvorak | 562/466 |
| 4,571,333 | 2/1986 | Hsiao et al. | 424/22 |
| 4,605,758 | 8/1986 | Schloemer | 562/418 |
| 4,609,766 | 9/1986 | Giordano et al. | 568/592 |
| 4,621,152 | 11/1986 | Berini | 562/401 |
| 4,623,736 | 11/1986 | Walker et al. | 549/369 |
| 4,654,438 | 3/1987 | Schloemer | 562/496 |
| 4,723,033 | 2/1988 | Erickson | 560/56 |
| 4,803,079 | 2/1989 | Hsiao et al. | 424/468 |
| 4,851,444 | 7/1989 | Sunshine et al. | 514/570 |
| 4,857,462 | 8/1989 | Maier et al. | 435/197 |
| 4,864,063 | 9/1989 | Piccolo et al. | 568/328 |
| 4,877,620 | 10/1989 | Loew et al. | 424/451 |
| 5,015,764 | 5/1991 | Manimaran et al. | 562/401 |
| 5,034,416 | 7/1991 | Smith | 514/568 |
| 5,220,053 | 6/1993 | Choudhury et al. | 562/401 |
| 5,221,765 | 6/1993 | Patil et al. | 562/401 |
| 5,235,095 | 8/1993 | Kadkhodayan et al. | 560/218 |
| 5,235,100 | 8/1993 | Choudhury et al. | 562/401 |
| 5,235,101 | 8/1993 | Patil et al. | 562/401 |
| 5,248,813 | 9/1993 | Manimaran et al. | 562/401 |
| 5,256,816 | 10/1993 | Murray et al. | 562/401 |
| 5,278,337 | 1/1994 | Manimaran et al. | 562/401 |
| 5,278,338 | 1/1994 | Trace | 562/401 |
| 5,574,183 | 11/1996 | Patil et al. | 562/401 |

*Primary Examiner*—Paul J. Killos
*Attorney, Agent, or Firm*—Philip M. Pippenger

[57] ABSTRACT

Sodium (S)-2-(6-methoxy-2-naphthyl)propionate of at least 99% chiral purity is formed from (S)-2-(6-methoxy-2-naphthyl)propionic acid having a chiral purity of at least about 82%, but below 99%. This is done by distilling a two-phase mixture formed from (i) the (S)-2-(6-methoxy-2-naphthyl)propionic acid, (ii) water, (iii) sodium hydroxide, sodium oxide and/or at least one basic inorganic sodium salt in an amount proportioned to neutralize from about 50 to about 99% of said acid, and optionally but preferably, (iv) an inert organic solvent that has a boiling point of at least 95° C. at 760 mm Hg such that water is removed from said mixture, and a pot residue containing sodium (S)-2-(6-methoxy-2-naphthyl)propionate of at least 99% chiral purity is formed.

33 Claims, No Drawings

PREPARATION OF HIGH PURITY SODIUM (S)-2(6-METHOXY-2-NAPHTHYL) PROPIONATE

This invention relates to preparation of high purity sodium (S)-2-(6-methoxy-2-naphthyl)propionate, a nonsteroidal antiinflammatory agent known generically as naproxen sodium.

To satisfy commercial specifications, naproxen sodium of chiral purity of 99% or more of the S-enantiomer is desired.

It has been found that, surprisingly, when neutralizing (S)-2-(6-methoxy-2-naphthyl)propionic acid having a chiral purity below 99% with less than a stoichiometric amount of aqueous sodium hydroxide solution to form naproxen sodium, it is possible to increase the chiral purity of the naproxen sodium to 99% or more by removing the water by use of a suitable organic solvent, or simply by distilling off water from an aqueous solution.

This invention makes it possible to produce high purity sodium (S)-2-(6-methoxy-2-naphthyl)propionate by carrying the distillation to an end point of at least 95° C. at atmospheric pressure (760 mm Hg). Pursuant to one such embodiment of the invention, an inert organic solvent that has a boiling point of at least 95° C. at atmospheric pressure and that does not form an azeotropic mixture with water that boils below 95 ° C. at atmospheric pressure is used. In another such embodiment, an inert organic solvent that has a boiling point of at least 95° C. at atmospheric pressure but that does form an azeotropic mixture with water that boils below 95° C. at atmospheric pressure is used, and in this case the amount of such solvent is in excess of the amount required to remove all of the water present. Both such embodiments produce high purity anhydrous sodium (S)-2-(6-methoxy-2-naphthyl)propionate. In a third embodiment, no inert organic solvent is used. Instead, the water is distilled off until solid higher purity sodium (S)-2-(6-methoxy-2-naphthyl)propionate is formed.

Thus, in accordance with this invention sodium (S)-2-(6-methoxy-2-naphthyl)propionate of at least 99% chiral purity is prepared by a process which comprises:

a) forming a two-phase mixture from (i) (S)-2-(6-methoxy-2-naphthyl)propionic acid having a chiral purity of at least about 82%, but below 99%, (ii) water, (iii) sodium hydroxide, sodium oxide and/or at least one basic inorganic sodium salt in an amount proportioned to neutralize from about 50 to about 99% of said acid, and optionally, but preferably, (iv) an inert organic solvent that has a boiling point of at least 95° C. at 760 mm Hg; and b) removing water from said mixture by distillation in an amount such that a pot residue containing sodium (S)-2-(6-methoxy-2-naphthyl)propionate of at least 99% chiral purity is formed.

The two-phase mixture formed in a) above can be liquid-liquid or a solid-liquid two-phase system. For example, the mixture as formed may initially be a system having two liquid phases, and as water is removed in b) above (typically by stripping it off), the system will become a solid-liquid two-phase system. Alternatively, it is possible to initially form a solid-liquid two-phase mixture which will remain a solid-liquid two-phase mixture during the water removal.

The chiral purity of the initial free acid used is preferably in the range of 90% to 98.5%, and most preferably in the range of about 97% to 98.5%, as this minimizes the thermal requirements for the overall chiral purity enrichment process.

Suitable inert organic solvents some of which form azeotropic mixtures with water boiling below 95° C. include benzene, toluene, xylene, ethyl acetate, propionitrile, chlorobenzene, hexane, octane, decane, dibutyl ether, anisole, and like substances.

Recovery of the naproxen sodium of increased chiral purity from the pot residue can be accomplished by separating the solids from the pot residue (distilland) remaining after the distillation, washing the solids with a suitable volatile inert organic solvent such as benzene, toluene, hexane, heptane, ethyl acetate, or the like, and then removing the solvent and drying the product, typically at reduced pressure, to leave purified dry naproxen sodium of a chiral purity of 99% or more. The separation and recovery of the solids from the pot residue is preferably carried out by centrifuging the pot residue, although other suitable methods of solids-liquid separation may be used. During this separation and recovery step two conditions should be observed and maintained to avoid contamination of the sodium (S)-2-(6-methoxy-2-naphthyl)propionate product being recovered. First, the temperature of the pot residue from which the solid, high chiral purity sodium (S)-2-(6-methoxy-2-naphthyl)propionate product is being separated should be kept high enough to keep in solution the low chiral purity sodium (S)-2-(6-methoxy-2-naphthyl)propionate that is already in solution in the organic solvent. Secondly, the unreacted excess of (S)-2-(6methoxy-2-naphthyl)propionic acid present in the pot residue should also be kept dissolved in the organic solvent. These two conditions can best be accomplished by centrifuging the pot residue at a temperature sufficiently high to keep both the low chiral purity sodium (S)-2-(6-methoxy-2-naphthyl)propionate and the free acid in solution in the organic solvent. The temperature used will depend on the organic solvent used and the relative proportions of organic solvent, low chiral purity sodium (S)-2-(6-methoxy-2-naphthyl)propionate, and free (S)-2-(6-methoxy-2-naphthyl)propionic acid. Thus in any given situation it is desirable to conduct a few simple laboratory experiments to measure (a) the solubility of several samples of sodium (S)-2-(6-methoxy-2-naphthyl)propionate of different known low chiral purities in the particular solvent at several appropriate temperatures, and (b) the solubility of the (S)-2-(6-methoxy-2-naphthyl)propionic acid in the particular solvent at several appropriate temperatures. From this information one can ascertain the amount of the particular organic solvent to be used and the temperature to be used with the projected amounts of low chiral purity sodium (S)-2-(6-methoxy-2-naphthyl)propionate and of the free (i.e., unneutralized or excess) (S)-2-(6-methoxy-2-naphthyl) propionic acid that is to be present in the pot residue. As an example, when using toluene or other higher boiling liquid aromatic hydrocarbons as the organic solvent, the foregoing two conditions can be satisfied by keeping the temperature of the pot residue at about 60° C. or above (e.g., 60° to 90° C.) during centrifugation.

Water-soluble inorganic basic sodium compounds that can be used to effect the partial neutralization of the initial (S)-2-(6-methoxy-2-naphthyl)propionic acid include, for example, sodium hydroxide, sodium oxide, sodium carbonate, sodium bicarbonate, sodium amide, and similar water-soluble basic inorganic sodium compounds, whether used singly or in combinations of two or more such compounds. Use of sodium oxide is preferred. Use of sodium hydroxide is particularly preferred because of its low cost, strong basicity, and ready availability from numerous suppliers.

Chiral purity of sodium (S)-2-(6-methoxy-2-naphthyl) propionate can be determined by use of the procedure of Hermansson and Erikson, entitled "Direct Liquid Chromatographic Resolution of Acidic Drugs Using A Chiral Alpha-Acid Glycoprotein Column" and appearing in *Journal of Liquid Chromatography*, 1986, 9(2&3), 621–639, with the following slight modifications:

Flow: 1.2 mL/min.

Detection: 225 nm

Injection volume: 1 μL

Sample concentration: 300 ppm dissolved in the mobile phase.

Column: Chiral AGP100-4 (alpha-glycoprotein) 4×100 mm (available from

Advanced Separation Technologies).

The following example, wherein all percentages are by weight, illustrates the practice and advantages of this invention, and is not to be construed as constituting a limitation on the invention. It will be noted that the initial mixture of (S)-2-(6-methoxy-2-naphthyl)propionic acid was produced from materials of known chiral purity in order to form an impure starting material for use in demonstrating the process of this invention.

EXAMPLE (S)-2-(6-methoxy-2-naphthyl)propionic acid having a chiral purity of 99.36% S-enantiomer (98.28 grams) and racemic 2-(6-methoxy-2-naphthyl)propionic acid (1.77 grams) were added to a mixture of toluene (403 grams) and water (7.97 grams). After heating to 85° C., 0.38 gram of water was cut (drained out) from the mixture. Aqueous 50% sodium hydroxide solution (32.31 grams) was fed with a syringe pump over a 57-minute period. The resulting reaction slurry was agitated at 85°–86° C. for 22 minutes. The temperature was increased slowly to 100° C. in 436 minutes during which water was azeotropically removed with a Dean-Stark trap. The residual product mixture was centrifuged in a basket centrifuge at 60° C. and washed with toluene (203.8 grams) preheated to 60° C. The naproxen sodium product was dried in a vacuum oven at 80° C. for 2 hours. The weight of the dried naproxen sodium product was 90.01 grams, and its chiral purity was 99.23% S-enantiomer. Therefore, the process of this invention increased the chiral purity of the initial mixture from 98.49% to 99.23%.

It is to be understood that the components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing sodium (S)-2-(6-methoxy-2-naphthyl)propionate of at least 99% chiral purity, which process comprises:
    a) forming a two-phase mixture from (i) (S)-2-(6-methoxy-2-naphthyl)propionic acid having a chiral purity of at least about 82%, but below 99%, (ii) water, (iii) sodium hydroxide, sodium oxide and/or at least one basic inorganic sodium salt in an amount proportioned to neutralize from about 50 to about 99% of said acid, and optionally, (iv) an inert organic solvent that has a boiling point of at least 95° C. at 760 mm Hg; and
    b) removing water from said mixture by distillation in an amount such that a pot residue containing sodium (S)-2-(6-methoxy-2-naphthyl)propionate of at least 99% chiral purity is formed.

2. A process according to claim 1 wherein said (S)-2-(6-methoxy-2-naphthyl)propionic acid has a chiral purity in the range of about 90% to 98.5%.

3. A process according to claim 1 wherein said (S)-2-(6-methoxy-2-naphthyl)propionic acid has a chiral purity in the range of about 97% to 98.5%.

4. A process according to claim 1 wherein (iii) is sodium oxide or sodium hydroxide, or both.

5. A process according to claim 1 wherein said (S)-2-(6-methoxy-2-naphthyl)propionic acid has a chiral purity in the range of about 97% to 98.5%, and wherein (iii) is sodium oxide or sodium hydroxide, or both.

6. A process according to claim 5 wherein said inert organic solvent is present in said two-phase mixture and wherein sodium (S)-2-(6-methoxy-2-naphthyl)propionate of at least 99% chiral purity is recovered from said pot residue by centrifuging the pot residue at a temperature that keeps (a) sodium (S)-2-(6-methoxy-2-naphthyl)propionate of less than 99% chiral purity, and (b) free (S)-2-(6-methoxy-2-naphthyl)propionic acid in solution in said organic solvent.

7. A process of preparing sodium (S)-2-(6-methoxy-2-naphthyl)propionate of at least 99% chiral purity, which process comprises:

distilling a two-phase mixture formed from (i) (S)-2-(6-methoxy-2-naphthyl)propionic acid having a chiral purity of at least about 82%, but below 99%, (ii) water, (iii) sodium hydroxide, sodium oxide and/or at least one basic inorganic sodium salt in an amount proportioned to neutralize from about 50 to about 99% of said acid, and optionally, (iv) an inert organic solvent that has a boiling point of at least 95° C. at 760 mm Hg such that water is removed from said mixture and a pot residue containing sodium (S)-2-(6-methoxy-2-naphthyl)propionate of at least 99% chiral purity is formed.

8. A process according to claim 7 wherein said (S)-2-(6-methoxy-2-naphthyl)propionic acid has a chiral purity in the range of about 90% to 98.5%.

9. A process according to claim 7 wherein said (S)-2-(6-methoxy-2-naphthyl)propionic acid has a chiral purity in the range of about 97% to 98.5%.

10. A process according to claim 7 wherein (iii) is sodium oxide or sodium hydroxide, or both.

11. A process according to claim 8 wherein said inert organic solvent is present in said two-phase mixture and wherein sodium (S)-2-(6-methoxy-2-naphthyl)propionate of at least 99% chiral purity is recovered from said pot residue by centrifuging the pot residue at a temperature that keeps (a) sodium (S)-2-(6-methoxy-2-naphthyl)propionate of less than 99% chiral purity, and (b) free (S)-2-(6-methoxy-2-naphthyl)propionic acid in solution in said organic solvent.

12. A process of preparing sodium (S)-2-(6-methoxy-2-naphthyl)propionate of at least 99% chiral purity, which process comprises:
   a) forming a two-phase mixture from (i) (S)-2-(6-methoxy-2-naphthyl)propionic acid having a chiral purity of at least about 82%, but below 99%, (ii) water, (iii) sodium hydroxide, sodium oxide and/or at least one basic inorganic sodium salt in an amount proportioned to neutralize from about 50 to about 99% of said acid, and (iv) an inert organic solvent that has a boiling point of at least 95° C. at 760 mm Hg; and
   b) removing water from said mixture by distillation in an amount such that a pot residue containing sodium (S)-2-(6-methoxy-2-naphthyl)propionate of at least 99% chiral purity is formed.

13. A process according to claim 12 wherein said (S)-2-(6-methoxy-2-naphthyl)propionic acid has a chiral purity in the range of about 90% to 98.5%.

14. A process according to claim 12 wherein said (S)-2-(6-methoxy-2-naphthyl)propionic acid has a chiral purity in the range of about 97% to 98.5%.

15. A process according to claim 12 wherein sodium (S)-2-(6-methoxy-2-naphthyl)propionate of at least 99% chiral purity is recovered from said pot residue by centrifuging the pot residue at a temperature that keeps (a) sodium (S)-2-(6-methoxy-2-naphthyl)propionate of less than 99% chiral purity, and (b) free (S)-2-(6-methoxy-2-naphthyl)propionic acid in solution in said organic solvent.

16. A process according to claim 12 wherein said organic solvent is a hydrocarbon solvent.

17. A process according to claim 16 wherein said hydrocarbon solvent is an aromatic hydrocarbon solvent.

18. A process according to claim 16 wherein (iii) is sodium oxide or sodium hydroxide, or both.

19. A process according to claim 18 wherein said organic solvent is a hydrocarbon solvent.

20. A process according to claim 19 wherein said hydrocarbon solvent is an aromatic hydrocarbon solvent.

21. A process according to claim 20 wherein sodium (S)-2-(6-methoxy-2-naphthyl)propionate of at least 99% chiral purity is recovered from said pot residue by centrifuging the pot residue at a temperature that keeps (a) sodium (S)-2-(6-methoxy-2-naphthyl)propionate of less than 99% chiral purity, and (b) free (S)-2-(6-methoxy-2-naphthyl)propionic acid in solution in said organic solvent.

22. A process according to claim 20 wherein said aromatic hydrocarbon solvent is entirely or predominately toluene.

23. A process of preparing sodium (S)-2-(6-methoxy-2-naphthyl)propionate of at least 99% chiral purity, which process comprises:
   distilling a two-phase mixture formed from (i) (S)-2-(6-methoxy-2-naphthyl)propionic acid having a chiral purity of at least about 82%, but below 99%, (ii) water, (iii) sodium hydroxide, sodium oxide and/or at least one basic inorganic sodium salt in an amount proportioned to neutralize from about 50 to about 99% of said acid, and, optionally, (iv) an inert organic solvent that has a boiling point of at least 95° C. at 760 mm Hg such that water is removed from said mixture and a pot residue containing sodium (S)-2-(6-methoxy-2-naphthyl)propionate of at least 99% chiral purity is formed.

24. A process according to claim 23 wherein said (S)-2-(6-methoxy-2-naphthyl)propionic acid has a chiral purity in the range of about 97% to 98.5%.

25. A process according to claim 24 wherein the organic solvent is present in said two-phase mixture and is an aromatic hydrocarbon solvent.

26. A process according to claim 25 wherein (iii) is sodium oxide or sodium hydroxide, or both.

27. A process according to claim 25 wherein (iii) is sodium hydroxide, and wherein the organic solvent is entirely or predominately toluene.

28. A process according to claim 23 wherein said inert organic solvent is present in said two-phase mixture and wherein sodium (S)-2-(6-methoxy-2-naphthyl)propionate of at least 99% chiral purity is recovered from said pot residue by centrifuging the pot residue at a temperature that keeps (a) sodium (S)-2-(6-methoxy-2-naphthyl)propionate of less than 99% chiral purity, and (b) free (S)-2-(6-methoxy-2-naphthyl)propionic acid in solution in said organic solvent.

29. A process of preparing sodium (S)-2-(6-methoxy-2-naphthyl)propionate of at least 99% chiral purity, which process comprises:
   distilling a two-phase mixture containing (i) (S)-2-(6-methoxy-2-naphthyl)propionic acid having a chiral purity of at least about 82%, but below 99%, (ii) water, (iii) sodium hydroxide, sodium oxide and/or at least one basic inorganic sodium salt in an amount proportioned to neutralize from about 50 to about 99% of said acid, and optionally, (iv) an inert organic solvent that has a boiling point of at least 95° C. at 760 mm Hg such that water is removed from said mixture and a pot residue containing sodium (S)-2-(6-methoxy-2-naphthyl)propionate of at least 99% chiral purity is formed; said substances (i), (ii), and (iii), and also (iv) if present, being in whatever chemical form(s) and composition(s) as they exist in said mixture before, during and after the distillation, irrespective of whatever change or changes, if any, in chemical form and/or composition one or more of such substances may undergo during such distillation.

30. A process according to claim 29 wherein said (S)-2-(6-methoxy-2-naphthyl)propionic acid, in whatever chemical form(s) and composition(s) as it exists in said mixture, has a chiral purity in the range of about 97% to 98.5%.

31. A process according to claim 30 wherein the organic solvent is present in said two-phase mixture and is an aromatic hydrocarbon solvent in whatever chemical form(s) and composition(s) as it exists in said mixture.

32. A process according to claim 31 wherein (iii) is sodium oxide or sodium hydroxide, or both, in whatever chemical form(s) and composition(s) as it exists or they exist in said mixture.

33. A process according to claim 31 wherein (iii) is sodium hydroxide in whatever chemical form(s) and composition(s) as it exists in said mixture, and wherein the organic solvent is entirely or predominately toluene in whatever chemical form(s) and composition(s) as it exists in said mixture.

* * * * *